United States Patent [19]
Hsieh

[11] Patent Number: 5,491,735
[45] Date of Patent: Feb. 13, 1996

[54] IMAGE RECONSTRUCTION APPARATUS AND METHOD FOR HELICAL SCANNING

[75] Inventor: Jiang Hsieh, Waukesha, Wis.

[73] Assignee: General Electric Company, Milwaukee, Wis.

[21] Appl. No.: 361,984

[22] Filed: Dec. 22, 1994

[51] Int. Cl.⁶ .......................... A61B 6/03; G01N 23/083
[52] U.S. Cl. ................. 378/15; 378/901; 364/413.17
[58] Field of Search .................... 378/4, 15, 901; 364/413.17, 413.18

[56] References Cited

U.S. PATENT DOCUMENTS

| | | | |
|---|---|---|---|
| 4,580,219 | 4/1986 | Pelc et al. | 364/413.21 |
| 4,789,929 | 12/1988 | Nishimurs et al. | 364/413.15 |
| 5,090,037 | 2/1992 | Toth et al. | 378/4 |
| 5,208,746 | 5/1993 | King et al. | 364/413.16 |
| 5,216,601 | 6/1993 | Crawford et al. | 364/413.16 |
| 5,233,518 | 8/1993 | King et al. | 364/413.18 |
| 5,262,946 | 11/1993 | Heuscher | 364/413.18 |
| 5,265,142 | 11/1993 | Hsieh | 378/4 |
| 5,270,923 | 12/1993 | King et al. | 364/413.13 |
| 5,291,402 | 3/1994 | Pfoh | 364/413.14 |
| 5,396,418 | 3/1995 | Heuscher | 364/413.18 |
| 5,430,783 | 7/1995 | Hu et al. | 378/15 |

OTHER PUBLICATIONS

C. R. Crawford, K. F. King, H. Hu, Fast Reconstruction of Overlapped Sections with helical CT.RSNA 1993 (no month).

E–Mail Letter Re: New Siemens Scanner Again, Jul. 21, 1994 (portion redacted).

*Primary Examiner*—David P. Porta
*Assistant Examiner*—David Vernon Bruce
*Attorney, Agent, or Firm*—John S. Beulick; John H. Pilarski

[57] ABSTRACT

The present invention, in one form, utilizes a region of reconstruction ROR in reconstructing an image from projection data. Particularly, once the region of reconstruction is established, a weighting function which is either a linear interpolation or a non-interpolation can be used. If $3\pi$ of projection data is used, the weighting function can be divided into three parts. Each part corresponds to $\pi$ projection views. For a 50% overlapped reconstruction, the entire weighting functions advance $\pi$ degrees at a time, which synchronizes very well with the boundaries of the weighting functions. Section $1(S_1)$ will contain projection views from 0 to $\pi$, section 2 ($S_2$) contains views from $\pi$ to $2\pi$, and section 3 ($S_3$) contains views from $2\pi$ to $3\pi$. In section $S_1$, the weighting function is a ramp-up function, in section $S_2$ the weighting function is a constant, and in section $S_3$ the weighting function is ramped down.

15 Claims, 3 Drawing Sheets

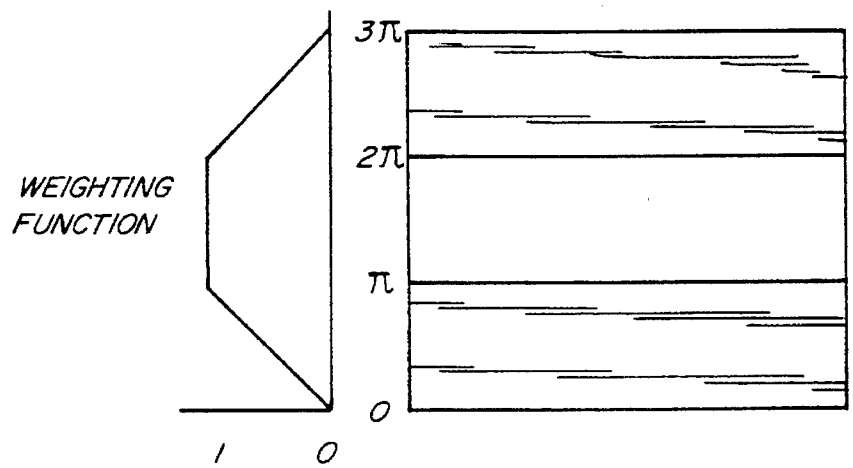

Fig. 5

| MEMORY 1 | MEMORY 2 | MEMORY 3 | MEMORY LOCATION OF THE FINAL IMAGE |
|---|---|---|---|
| $\triangle^1 + \square^2 + \triangleright^3$ | $\triangle^2 + \square^3$ | $\square^3 - \triangleright^3 = \triangle^3$ | 1 |
| $\square^4 - \triangleright^4 = \triangle^4$ | $\triangle^2 + \square^3 + \triangleright^4$ | $\triangle^3 + \square^4$ | 2 |
| $\triangle^4 + \square^5$ | $\square^5 - \triangleright^5 = \triangle^5$ | $\triangle^3 + \square^4 + \triangleright^5$ | 3 |
| $\triangle^4 + \square^5 + \triangleright^6$ | $\triangle^5 + \square^6$ | $\square^6 - \triangleright^6 = \triangle^6$ | 1 |

Fig. 6

IMAGE RECONSTRUCTION APPARATUS AND METHOD FOR HELICAL SCANNING

FIELD OF THE INVENTION

This invention relates generally to computed tomography (CT) imaging and more particularly, to the reconstruction of images from projection data acquired from a helical scan with improved quality image.

BACKGROUND OF THE INVENTION

In CT systems, an x-ray source projects a fan-shaped beam which is collimated to lie within an X-Y plane of a Cartesian coordinate system, termed the "imaging plane". The x-ray beam passes through the object being imaged, such as a patient, and impinges upon a linear array of radiation detectors. The intensity of the transmitted radiation is dependent upon the attenuation of the x-ray beam by the object. Each detector of the linear array produces a separate electrical signal that is a measurement of the beam attenuation. The attenuation measurements from all the detectors are acquired separately to produce a transmission profile.

The x-ray source and the linear detector array in a CT system are rotated with a gantry within the imaging plane and around the object so that the angle at which the x-ray beam intersects the object constantly changes. A group of x-ray attenuation measurements from the detector array at one gantry angle is referred to as a "view". A "scan" of the object comprises a set of views made at different gantry angles during one revolution of the x-ray source and detector. In an axial scan, data is processed to construct an image that corresponds to a two dimensional slice taken through the object. One method for reconstructing an image from a set of data is referred to in the art as the filtered backprojection technique. This process converts the attenuation measurements from a scan into integers called "CT numbers" or "Hounsfield units", which are used to control the brightness of a corresponding pixel on a cathode ray tube display.

A reduction in scan time can be achieved by translating a patient in the z-axis synchronously with the rotation of the gantry. The combination of constant patient translation along the z-axis during the rotation of the gantry and acquisition of projection data is known as helical scanning. Helical scanning is described, for example, in U.S. Pat. No. 5.233.518 which is assigned to the present assignee. In addition to reduced scanning time, helical scanning provides other advantages such as better control of contrast, improved image reconstruction at arbitrary locations, and better three-dimensional images.

Helical image reconstruction algorithms include constant weighting and variable weighting approaches. Constant weighting refers to the weighting schemes in which the weights do not change as a function of the detector channels. Therefore, for each view, a scalar is multiplied to each element in the projection. A variable weighting scheme applies weights that are a function of both the view angle and the detector channel. The majority of helical reconstruction algorithms utilize variable weighting schemes.

In general, the constant weighting schemes are simpler to implement and the data is easier to process. The image quality generated by constant weighting algorithms, however, may be somewhat inferior to that produced by the variable weighting schemes. On the other hand, the variable weighting schemes are more complex to implement. Since the weights are channel dependent, the weighting step and the filtering-backprojection steps are not interchangeable. That is, a backprojection of the filtration of the weighted projection does not equal to the scaled version of the unweighted filtration and backprojection. Therefore, in order to generate an overlapped image in a variable weighting scheme, the projections have to be re-filtered and back-projected.

There exists a need for a helical image reconstruction algorithm that produces images having a quality equivalent or close to the images produced by variable weighting schemes but is simple to implement as with the constant weighting schemes.

SUMMARY OF THE INVENTION

The present invention, in one form, utilizes a region of reconstruction ROR in reconstructing an image from projection data. Particularly, once the projection data array is created, a region of reconstruction is established. A weighting function which is either a linear interpolation or a non-linear interpolation is used to assign weights to the data elements. With linear interpolation, for projection data inside the ROR, no weighting (or a weight of one) is assigned to such projection data. As the projection plane moves away from the ROR, less weight is assigned to the projection data. Consequently, the first projection and the last projection will be assigned a weight of zero.

To avoid artifacts, a complementary weighting scheme may be applied to the projection pairs. The sum of the weights of the corresponding projection pairs should be one. Because of the weighting scheme, more than $2\pi$ of projection data is required to generate a single image. If $3\pi$ of projection data is used, the weighting function can be divided into three parts. Each part corresponds to $\pi$ projection views. For a 50% overlapped reconstruction, the entire weighting functions advance $\pi$ degrees at a time, which synchronizes very well with the boundaries of the weighting functions. Section 1($S_1$) contains projection views from 0 to $\pi$, section 2 ($S_2$) contains views from $\pi$ to $2\pi$, and section 3 ($S_3$) contains views from $2\pi$ to $3\pi$. In section $S_1$, the weighting function is a ramp-up function, in section $S_2$ the weighting function is a constant, and in section $S_3$ the weighting function is ramped down. For each projection, the weighting operation and the filtering-backprojection operations are interchangeable. That is, if a view is used as $S_2$ to generate image number 1 and is used again as $S_1$ to generate image number 2, no filtering and backprojection are needed. Its contribution to image number 2 is a simple scalar multiplication of its contribution to image number 1.

The present invention provides a helical image reconstruction algorithm that produces images having a quality equivalent or close to the images produced by variable weighting schemes. The present invention, however, is much simpler to implement than such variable weighting schemes.

BRIEF DESCRIPTION OF THE DRAWINGS

FIG. 5 is a Radon space diagram for $3\pi$ of projection data.

FIG. 6 illustrates one form of the present algorithm.

DETAILED DESCRIPTION OF THE DRAWINGS

Figure 1:
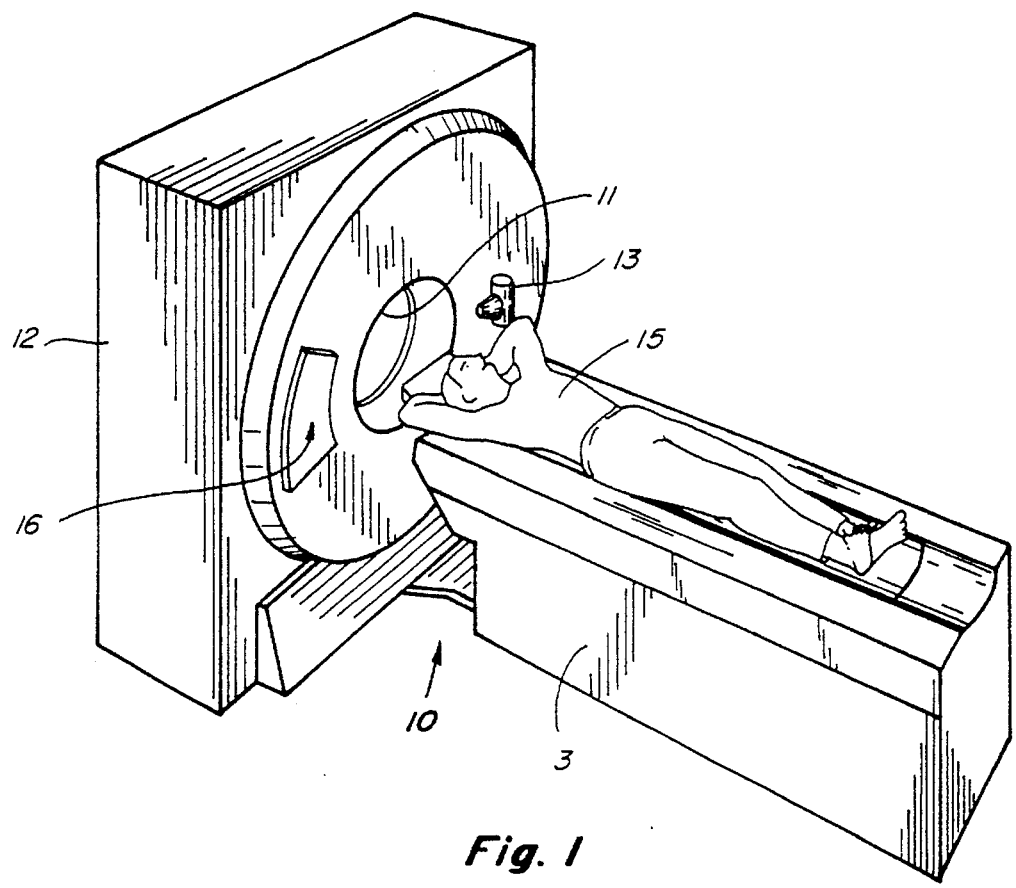
FIG. 1 is a pictorial view of a CT imaging system in which the present invention may be employed.
Figure 2:
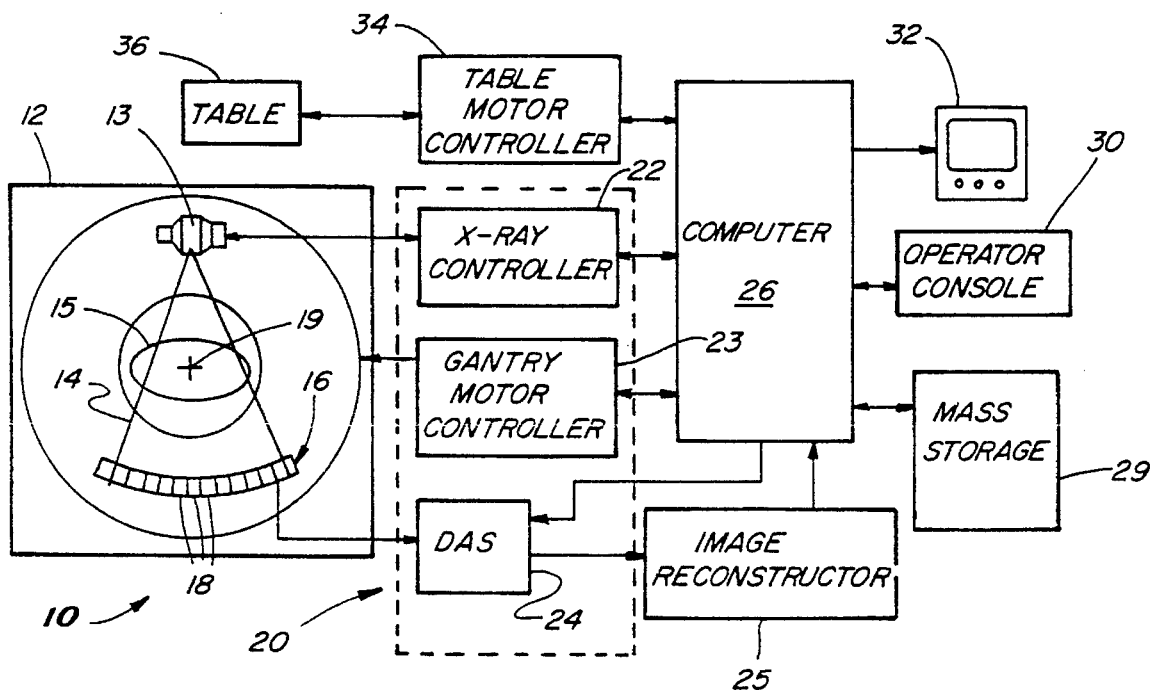
FIG. 2 is a block schematic diagram of the CT imaging system illustrated in FIG. 1.

With reference to FIGS. 1 and 2, a computed tomography (CT) imaging system 10 includes a gantry 12 representative of a "third generation" CT scanner. Gantry 12 has an x-ray source 13 that projects a beam of x-rays 14 toward a detector array 16 on the opposite side of gantry 12. Detector array 16 is formed by two rows of detector elements 18 which together sense the projected x-rays that pass through a medical patient 15. Each detector element 18 produces an electrical signal that represents the intensity of an impinging x-ray beam and hence the attenuation of the beam as it passes through patient 15. During a scan to acquire x-ray projection data, gantry 12 and the components mounted thereon rotate about a center of rotation 19.

Rotation of gantry 12 and the operation of x-ray source 13 are governed by a control mechanism 20 of CT system 10. Control mechanism 20 includes an x-ray controller 22 that provides power and timing signals to x-ray source 13 and a gantry motor controller 23 that controls the rotational speed and position of gantry 12. A data acquisition system (DAS) 24 in control mechanism 20 samples analog data front detector elements 18 and converts the data to digital signals for subsequent processing. An image reconstructor 25 receives sampled mid digitized x-ray data from DAS 24 and performs high speed image reconstruction. The reconstructed image is applied as an input to a computer 26 which stores the image in a mass storage device 29.

Computer 26 also receives commands and scanning parameters from an operator via console 30 that has a keyboard. An associated cathode ray tube display 32 allows the operator to observe the reconstructed image and other data from computer 26. The operator supplied commands and parameters are used by computer 26 to provide control signals and information to DAS 24, x-ray controller 22 and gantry motor controller 23. In addition, computer 26 operates a table motor controller 34 which controls a motorized table 36 to position patient 15 in gantry 12.

In reconstructing an image slice, typically a projection data array is created. Once the array is created, the data elements within the array are assigned weights. The weighted data is then used to created a weighted projection data array. Using the weighted projection data array, the data is filtered and back projected. An image data array is created as a result of the filtering and backprojection.

Figure 3:
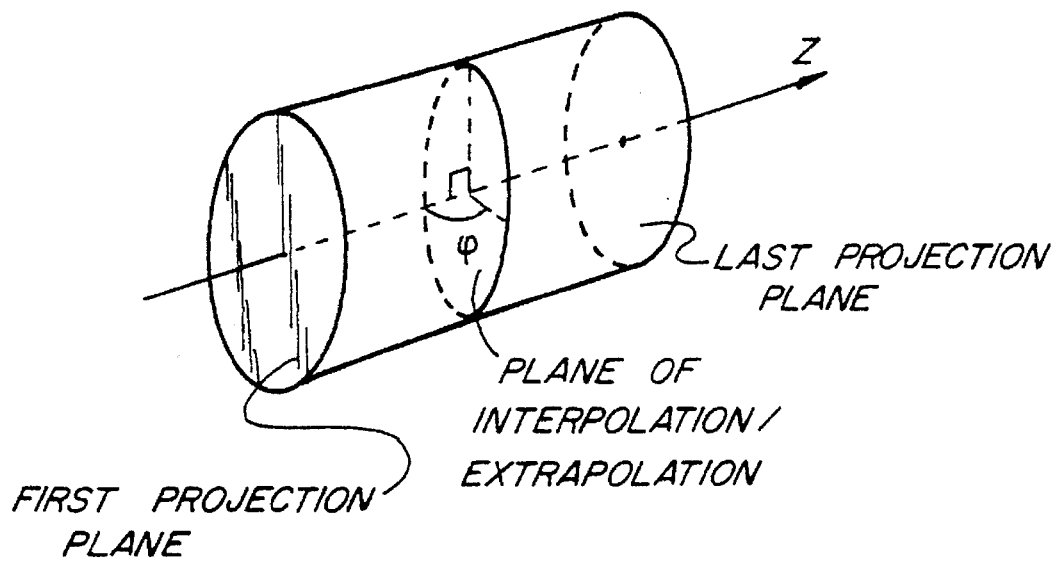
FIG. 3 illustrates a plane of reconstruction (POR).

An important consideration in weighting the data is the plane of reconstruction (POR). In known algorithms, the POR is either perpendicular or non-perpendicular to the axis of rotation. The plane can be either flat or warped. All of the sampling pairs (two redundant samples) are interpolated to a unique location in x as shown in FIG. 3. Although the intent of the interpolation is to estimate a set of consistent "axial" projections at the POR, the complexity of the object and the variation in the beam profile prevent an accurate estimation.

Figure 4:
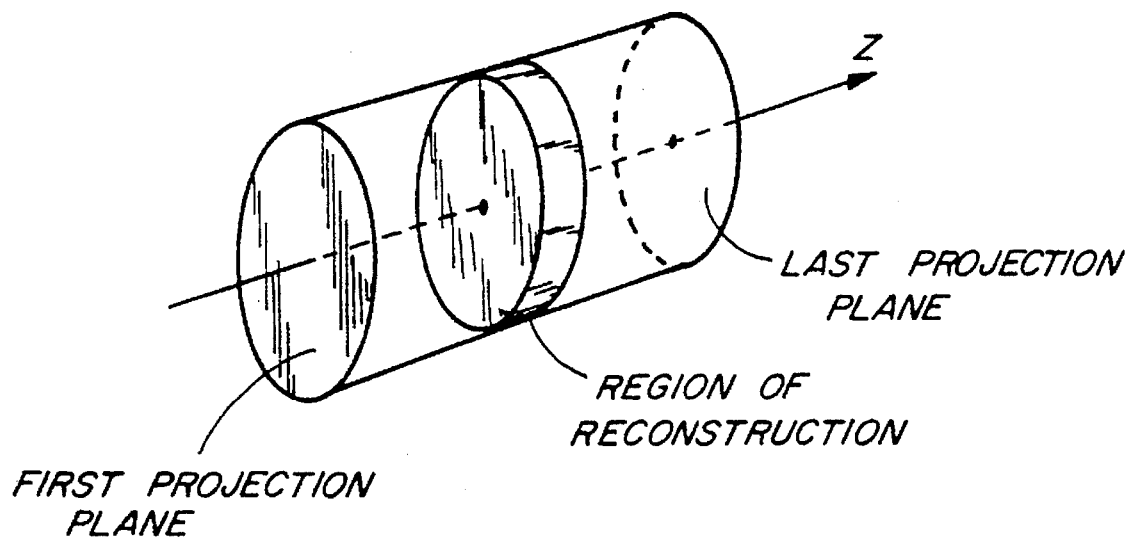
FIG. 4 illustrates a region of reconstruction (ROR).

The present algorithm is based upon a region of reconstruction (ROR), as shown in FIG. 4, rather than a POR, to assign weights to the projection data. Once the ROR is established, the weighting function generation is very simple. Particularly, either a linear interpolation or non-linear interpolation can be used. With linear interpolation, a projection is acquired inside the ROR, no weighting (or a weight of one) is assigned to such projection data. As the projection plane moves away from the ROR, less weight is assigned to the projection data. Consequently, the first projection and the last projection (shown in FIG. 4) will be assigned a weight of zero.

To avoid artifacts, a complementary weighting scheme may be applied to the projection pairs. A projection pair is defined as two projections whose view angles are multiples of $2\pi$ apart. If the data were acquired in a cine mode (table increment is zero), the projection pair will represent redundant projections. The sum of the weights of the corresponding projection pairs should be one. Because of the weighting scheme, more than $2\pi$ of projection data is required to generate a single image.

For the case in which $3\pi$ projection is used, FIG. 5 shows the corresponding diagram in Radon space. The two shaded areas represent redundant projection samples. The projection pairs in this case are $2\pi$ apart. The middle unshaded region represents the ROR, which covers $\pi$ degree of span. The weights for each view is plotted to the left of the diagram. Linear weights are used for simplicity. The weighting function can be divided into three pans. Each part corresponds to $\pi$ projection views. For a 50% overlapped reconstruction, the entire weighting functions advance $\pi$ degrees at a time, which synchronizes very well with the boundaries of the weighting functions.

With respect to generating 50% overlapped images, the 50% overlapped images are generated by advancing the starting projection by $\pi$. For example, if an image is generated with a starting view angle of $\theta$, the next image should have a starting view angle of $\theta+\pi$.

The entire Radon space can be divided into 3 sections each contains $\pi$ views. Therefore, section $1(S_1)$ will contain projection views from 0 to $\pi$, section 2 $(S_2)$ contains views from $\pi$ to $2\pi$, and section 3 $(S_3)$ contains views from $2\pi$ to $3\pi$. In $S_1$, the weighting function is a ramp-up function, in section $S_2$ the weighting function is a constant, and in section $S_3$ the weighting function is ramped down. For each projection, the weighting operation and the filtering-backprojection operations are interchangeable. That is, if a view is used as $S_2$ to generate image number 1 and is used again as $S_1$ to generate image number 2, no filtering and backprojection are needed. Its contribution to image number 2 is a simple scalar multiplication of its contribution to image number 1.

For the ease of discussion, several symbols are defined below and used in FIG. 6. Particularly, a right triangle, RT, denotes an image generated by the ramp-up function in $S_1$. A square, SQ, and a left triangle, LT, denote images generate by weighting functions in $S_2$ and $S_3$, respectively. A superscript k denotes the kth $\pi$ view section in a helical scan. For example, $SQ^k$ represents an image generated with projection views from $(k-1)\pi$ to $k\pi$ with a constant weighting function used in $S_2$. With the notation, each final image is then the sum of three images: $RT^{k-1}+SQ^k+LT^{k+1}$. As indicated previously, no additional filtering and backprojection is required to generate from $RT^k$ to either $SQ^k$ or $LT^k$ as long as the backprojected value is properly scaled prior to the summation.

The following simple relationship exists between the three parts $RT^k+LT^k=SQ^k$. Therefore, by generating and storing two of the three weighted images, the third view can be recovered. For each section of $\pi$ projections, only two weighted images need to be generated and stored (only one filtering and one backprojection is required). The final image will then be the simple summations and substractions of these weighted images of the three adjacent sections.

The flow diagram set forth in FIG. 6 illustrates one of the possible ways of implementing the present algorithm. If the final image is 512 by 512 in size, the scheme requires three 512 by 512 size image memories. Other schemes, such as processing the weighted images off an image generation board, are contemplated. When off-board processing is performed, only two 512 by 512 memories are required.

As set forth above, the present invention is a simple interpolative algorithm, using $3\pi$ projection data. Images generated by the present algorithm are nearly equivalent to the ones generated by a known helical extrapolative (HE) algorithm in terms of z-axis profiles and shading artifacts. The present algorithm also is superior to that of the known HE algorithms in terms of improvement in noise. The present algorithm also performs better in terms of aliasing artifacts and imaging artifacts.

Importantly, the present algorithm can be implemented very efficiently to produce 50% overlapped images with little cost in computational time. Therefore, images can be reconstructed at nearly twice the rate that images are generated using known algorithms. Such increased rate is of significance with respect to increasing patient throughput and customer productivity.

From the preceding description of one embodiment of the present invention, it is evident that the objects of the invention are attained. Although the invention has been described and illustrated in detail, it is to be clearly understood that the same is intended by way of illustration and example only and is not to be taken by way of limitation. For example, the present algorithm could be implemented in multi-slice helical scanners. Accordingly, the spirit and scope of the invention are to be limited only by the terms of the appended claims.

What is claimed is:

1. A method of producing a tomographic image of an image object from data acquired in a helical scan, the data having been collected in a series of fan beam projections at a plurality of gantry angles about an axis and within an image plane, said method comprising the steps of:
   (a) creating a projection data array using the data collected in the helical scan;
   (b) creating a weighted data array by assigning weights to each data element in the projection data array, the weights being assigned by:
      (i) establishing a region of reconstruction;
      (ii) assigning each data element within the region of reconstruction a weight of one; and
      (iii) as the projection plane moves away from the region of reconstruction, assigning a lesser weight to each data element.

2. A method in accordance with claim 1 wherein assigning a lesser weight to each data element is performed using linear interpolation.

3. A method in accordance with claim 1 wherein assigning a lesser weight to each data element is performed using non-linear interpolation.

4. A method in accordance with claim 1 wherein $3\pi$ of projection data is collected.

5. A method in accordance with claim 4 wherein 50% overlapped images are to be generated and weights are assigned to the data elements in the projection data array by dividing the weighting function into three parts, each part corresponding to $\pi$ projection views.

6. A system for of producing a tomographic image of an object, said system comprising means for perforating a helical scan of the object and for collecting beam projection data during the helical scan from a series of fan beam projections at a plurality of gantry angles about an axis and within an image plane, said tomographic image system further comprising a data acquisition system configured to:
   (a) create a projection data array using the data collected in the helical scan;
   (b) create a weighted data array by assigning weights to each data element in the projection data array, the weights being assigned by:
      (i) establishing a region of reconstruction;
      (ii) assigning each data element within the region of reconstruction a weight of one; and
      (iii) as the projection plane moves away from the region of reconstruction, assigning a lesser weight to each data element.

7. A system in accordance with claim 6 wherein said data acquisition system is configured to assign a lesser weight to each data element in accordance by linear interpolation.

8. A system in accordance with claim 6 wherein said data acquisition system is configured to assign a lesser weight to each data element in accordance by non-linear interpolation.

9. A system in accordance with claim 6 wherein $3\pi$ of projection data is collected.

10. A system in accordance with claim 6 wherein 50% overlapped images are to be generated and weights are assigned to the data elements in the projection data array by dividing the weighting function into three parts, each part corresponding to $\pi$ projection views.

11. A data acquisition system for use in connection with a tomographic imaging system which performs a helical scan of an object and collects beam projection data during the helical scan from a series of fan beam projections at a plurality of gantry angles about an axis and within an image plane, said data acquisition system comprising:
   (a) means for creating a projection data array using the data collected in the helical scan;
   (b) means for creating a weighted data array by assigning weights to each data element in the projection data array, said weighted data array creating means being programmed to perform the steps of:
      (i) establishing a region of reconstruction;
      (ii) assigning each data element within the region of reconstruction a weight of one; and
      (iii) as the projection plane moves away from the region of reconstruction, assigning a lesser weight to each data element.

12. A data acquisition system in accordance with claim 11 wherein said weighted data array creating means assigns a lesser weight to each data element in accordance by linear interpolation.

13. A data acquisition system in accordance with claim 11 wherein said weighted data array creating means assigns a lesser weight to each data element in accordance by non-linear interpolation.

14. A data acquisition system in accordance with claim 11 wherein $3\pi$ of projection data is collected by the tomographic imaging system.

15. A data acquisition system in accordance with claim 11 wherein 50% overlapped images are to be generated and weights are assigned to the data elements in the projection data array by dividing the weighting function into three parts, each part corresponding to $\pi$ projection views.

* * * * *